United States Patent
Jhuboo et al.

(10) Patent No.: US 6,558,347 B1
(45) Date of Patent: May 6, 2003

(54) CONTROL DEVICE AND PROCESS FOR A PUMPING DEVICE

(75) Inventors: Abdel Nasser Jhuboo, Saint Etienne de Saint Geoirs (FR); Jean-Claude Rondelet, Saint Etienne de Crossey (FR)

(73) Assignee: Fresenius Vial SA, Brezins (FR)

( * ) Notice: Subject to any disclaimer, the term of this patent is extended or adjusted under 35 U.S.C. 154(b) by 0 days.

(21) Appl. No.: 09/511,405

(22) Filed: Jul. 3, 2000

(30) Foreign Application Priority Data

Feb. 23, 1999 (FR) .............................................. 99 02390

(51) Int. Cl.⁷ ............................................. A61M 31/00
(52) U.S. Cl. ............................. 604/67; 604/65; 604/151
(58) Field of Search ............................. 604/67, 65, 151, 604/152, 154, 120, 121; 128/DIG. 12; 417/63

(56) References Cited

U.S. PATENT DOCUMENTS

| | | | |
|---|---|---|---|
| 3,756,234 A | * 9/1973 | Kopp | ........................... 604/67 |
| 4,840,542 A | 6/1989 | Abbott | |
| 5,047,014 A | * 9/1991 | Mosebach et al. | ............. 604/67 |
| 5,096,385 A | * 3/1992 | Georgi et al. | ................. 604/67 |
| 5,103,211 A | 4/1992 | Daoud et al. | |
| 5,213,573 A | * 5/1993 | Sorich et al. | ......... 128/DIG. 12 |
| 5,336,053 A | 8/1994 | Wynkoop | |
| 5,356,378 A | * 10/1994 | Doan | ........................... 604/65 |
| 5,522,799 A | * 6/1996 | Furukawa | ..................... 604/65 |
| 5,609,576 A | * 3/1997 | Voss et al. | ..................... 604/67 |
| 5,807,322 A | * 9/1998 | Lindsey et al. | ............... 604/65 |
| 5,827,223 A | * 10/1998 | Butterfield | .................... 604/65 |
| 6,077,055 A | * 6/2000 | Vilks | ........................... 604/65 |
| 6,164,921 A | * 12/2000 | Moubayed et al. | ........... 604/67 |

FOREIGN PATENT DOCUMENTS

| | | |
|---|---|---|
| EP | 0 315 312 | 5/1989 |
| EP | 0 431 310 | 6/1991 |

\* cited by examiner

Primary Examiner—Henry Bennett
Assistant Examiner—Fadi H. Dahbour
(74) Attorney, Agent, or Firm—Kenyon & Kenyon

(57) ABSTRACT

A control process and device for a pump is described, comprising a pump equipped with a flexible tube used in a drop-by-drop infusion systems. The infusion tube can be blocked downstream of the pump when the pump is started. The pressure created in the section of the tube located between the pump and the blockage is measured. If there is a fault in the infusion system, such as a defective pump, poor positioning of the tube in the pump, blockage or rupture of the tube upstream of the pump, the increased pressure will result in anomalies that are detected.

13 Claims, 2 Drawing Sheets

CONTROL DEVICE AND PROCESS FOR A PUMPING DEVICE

The invention relates to a control process for pump device comprising a pump equipped with a flexible tube.

DESCRIPTION OF RELATED ART

In current medical practice, drop-by-drop infusion devices are used to administer solutions to patients at a relatively slow rate. These drop-by-drop devices comprise a tube connecting the container with the solution to the patient and a volumetric pump controlling the rate of flow. To ensure the patient's safety, it is essential that the flow of solution be controlled as it passes through the drop-by-drop device. To accomplish this, it is common to add to the pump a drop detector, generally comprising an optical detector connected to the drip chamber of the drop-by-drop device.

These detectors provide a high degree of safety and are able to detect underflow situations during which no drops are formed due, for example, to blockage of the tube, improper tube positioning in the pump, or reversal of the direction of the tube in the pump. The detectors also detect overflow situations during which drops flow too rapidly (the normal rate being approximately 20 drops per minute) or so rapidly that they form a continuous stream of solution, for example, as a result of tube rupture, poor tube positioning in the pump, or a pump defect.

Such drop detectors are highly sensitive and can trigger false alarms. Sometimes false data can be generated if the drip chamber is tilted or if drops are present on the wall of the drip chamber.

SUMMARY OF THE INVENTION

The present invention provides a control process for a pump device comprising a pump equipped with a flexible tube similar to those used for drop-by-drop infusion, that avoids the drawbacks of the known process and that uses a drop detector.

In one aspect, the invention is a control process for a pumping device that comprises a pump equipped with a flexible tube, the process comprising the steps of blocking said flexible tube by means of an occlusion device located downstream of said pump, starting said pump, and measuring an instantaneous pressure in a section of said flexible tube situated between said pump and said occlusion device. The process also includes adjusting said pump for a flow rate substantially equal to a maximum flow, performing a predetermined number of cycles, said number of cycles being at least equal to 1, stopping the pump, and triggering an alarm if the instantaneous pressure does not reach a threshold pressure value after the predetermined number of cycles.

In another aspect, the invention is a control device for a pumping device with a pump, comprising a flexible tube introduced into the pump, an occlusion device located downstream of said pump, and a pressure detector located between said pump and said occlusion device for measuring an instantaneous pressure.

In the process consistent with the invention, the flexible tube is obstructed by means of an occlusion device located downstream of the pump. The pump is started, and the instantaneous pressure $P_i$ is measured in the section of the tube located between the pump and the occlusion device. Before beginning the infusion, the infusion tube is blocked downstream of the pump and the pump is allowed to operate against this obstacle. Over pressure must be developed in the section of the tube located between the pump and the occlusion whose instantaneous value is measured.

If the pump is defective, during the pumping process a moment will occur during which there is no occlusion zone. In this case the over pressure will decrease, because of a reflux of liquid during the period in which the occlusion zone reappears. This loss of pressure can be detected by measuring the instantaneous pressure $P_i$.

When the pump is used for infusion, such defects can occur over a period of time during which the flow of solution will be uncontrolled, and such a situation repeats at regular intervals. Similarly, no over pressure will occur if the tube occlusion is located upstream of the pump, if the tube is poorly positioned in the pump, or if the direction of the tube in the pump is reversed.

According to the invention, the following steps are carried out:

a) the pump after being adjusted for a low rate close to the maximum flow rate, performs a number of predetermined cycles at least equal to one, after which it is stopped; and b) an alarm is triggered if the instantaneous pressure $P_i$, measured throughout step a, does not reach a threshold value $P_1$ by the end of step a.

To provide sufficient control, it is essential that the complete pumping cycle be monitored. For reasons of safety it is preferable that this take place for slightly more than one cycle, for example 1.1 cycles. If the pump is defective, the increased pressure will not be constant and the pump will fail to reach the threshold value at the end of the programmed rotation. The threshold value is calculated statistically for the individual pump type.

Another aspect of the invention involves carrying out the following additional steps when no alarm is triggered during step b described above. These steps are:

c) after being adjusted to an intermediate flow rate, the pump performs a number of predetermined cycles at least equal to 1 and is then stopped;

d) the minimum pressure, $P_{min}$, and maximum pressure, $P_{max}$, reached during the previous step, are measured; and e) an alarm is triggered if the minimum pressure $P_{min}$, or maximum pressure $P_{max}$, determined in step d do not reach the threshold values $P_2$ and $P_3$ respectively.

The intermediate flow rate chosen during step c can be used to detect any pressure loss while ensuring a relatively short control period, for example less than about 10 sec.

Another advantageous aspect of the process involves the triggering of an alarm during step 1 if the instantaneous pressure $P_i$ reaches a threshold value $P_4$ during step c. This involves detecting the formation of excessive over pressure capable of damaging the tube or pump.

To restore the infusion device to its normal operating state, an additional step g can be performed during which the pump is operated in the reverse direction for the exact number of cycles carried out during the previous steps. The occlusion device is also reopened at the end of the process if no alarm has been triggered. By taking this precaution, the control process can be accomplished both during an occlusion and at other times. This step is also necessary when the process is automated.

This process according to the invention is particularly well suited for application to finger pumps. However, it can also be used to detect a possible fracture of the pump support bracket.

A device for implementing the control process according to the invention can comprise, for example, a flexible tube, a pump in which the flexible tube is introduced, an occlusion device located downstream of the pump, and a pressure detector located between the pump and the occlusion device.

In a preferred embodiment the device for implementing the process incorporates a second pressure detector located upstream of the pump. This second assure detector can be used to detect an occlusion or rupture of the tube upstream of the pump, during the control process itself and during the infusion.

According to the invention, the device implementing the procedure can incorporate a control unit that can be used to control the opening and closing of the occlusion device; adjust the flow rate and on/off operation of the pump for the number of cycles determined in steps a and c; analyze the measured instantaneous pressure $P_i$ for steps b, d, e, and f; stop the pump whenever an alarm is generated; and run the pump in reverse for the number of cycles identified in the previous steps. The device for implementing the process can preferably operate automatically.

During operation, the control unit closes the tube occlusion device, adjusts the rate of flow of the pump to a value near the maximum, then causes it to operate for 1.1 cycles, for example, while analyzing the values supplied by the pressure detector. During the second stage of the process, the control unit adjusts the rate of flow of the pump to an intermediate value and causes the pump to operate for 1.1 cycles, for example, while analyzing the values for instantaneous pressure $P_i$ supplied by the pressure detector.

This same control unit can trigger alarms in the event these values are out of range. If, however, the control reveals no abnormalities, the unit causes the pump to operate in reverse for the same number of cycles it operated during the previous steps, and reopens the occlusion device. It is possible to program this control unit to perform the control process at the start of each infusion, and also during said infusion.

To increase safety it may be advantageous introduce the tube into e pump only in a predetermined direction. In this case, for example, the tube could include a device shaped like an arrow, indicating the direction of flow of the liquid, similar to the clamp described in French patent application 9901132.

BRIEF DESCRIPTION OF THE DRAWINGS

An example of the process according to the invention and a device for implementing said process are described below. In the Drawings.

DETAILED DESCRIPTION OF EMBODIMENTS OF THE INVENTION

Figure 1:
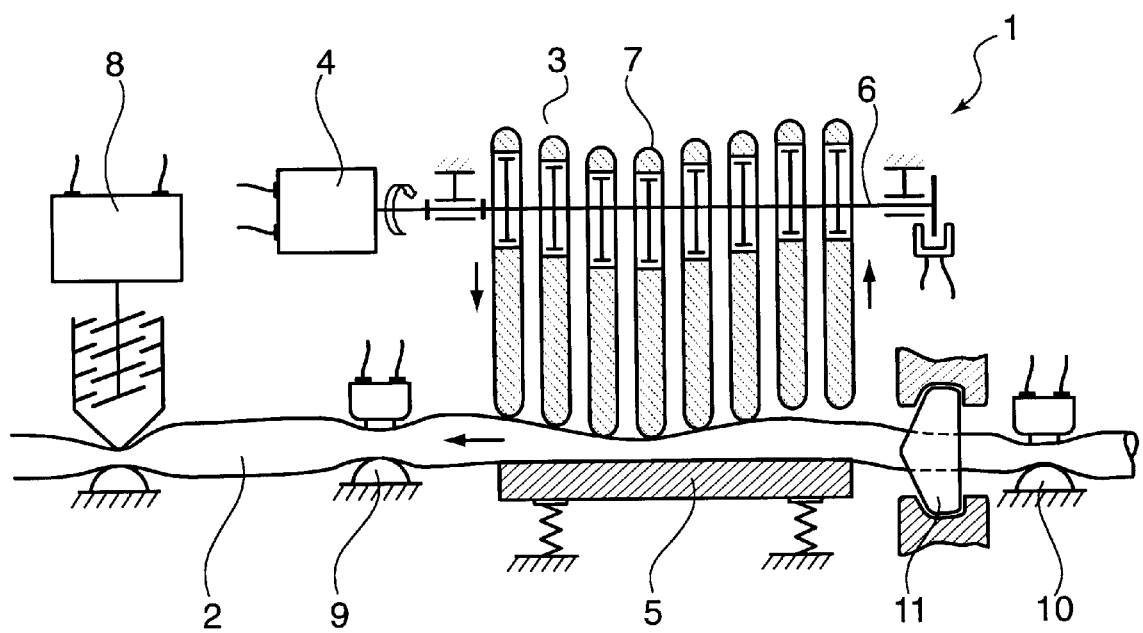
FIG. 1 is a schematic view showing a device for implementing the control process according to the invention.

As shown in FIG. 1, device 1 for implementing the control process in accordance with the invention preferably comprises a flexible tube 2 placed in finger pump 3, that is activated by motor 4 and equipped with support bracket 5, camshaft 6, and fingers 7. It also preferably comprises an occlusion device 8 located downstream of pump 3, pressure detector 9 located between pump 3 and occlusion device 8, second pressure detector 10 lifted upstream of pump 3, and automatic clamp 11 in the shape of an arrow.

The pressure detectors supply a voltage signal that is directly proportional to the pressure in the tube. They can be calibrated at two distinct pressures, for example, at 0 bar ($P_{0bar}$) and 1 bar ($P_{1bar}$).

Figure 2:
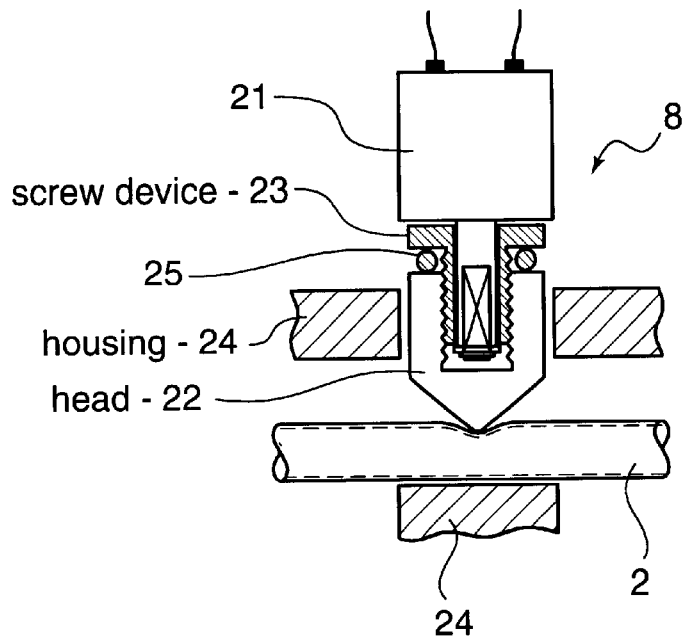
FIG. 2 is a side view of an occlusion device.

Occlusion device 8 may comprise DC motor 21, head 22 connected to motor 21 by threaded device 23, as shown in FIG. 2. To block tube 2, motor 21 turns, for example, in a clockwise direction, resulting in the displacement by translation of head 22. When the tube is compressed by head 22 against housing 24 of occlusion device 8, it is blocked. At this moment the motor's torque increases and the current in the motor increases proportionally. This current is measured and, when it has reached a limit value, the motor is stopped. To open the tube, motor 21 turns in the opposite direction. Rubber ring 25 located on screw device 23 at the end of the head's 22 travel can be completely retracted. The current in the motor increases, and when it has reached a limit value the motor is stopped.

Figure 3:
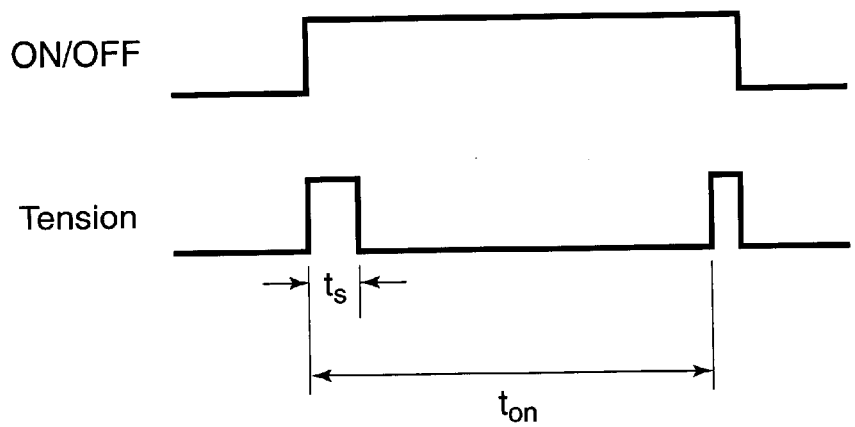
FIG. 3 is a diagram that represents a current measured in the occlusion device motor during opening or closing of said device.

Motor 21 is controlled by an H bridge. When the motor is started the current in the winding is high but preferably decreases after approximately 100 ms. The microprocessor analyzes the value of the current and generates an alarm if the time needed to reduce the current (1 sec) is greater than, for example, 300 ms, a sign that occlusion device 8 is malfunctioning. At the end of travel of head 22, either when it compresses flexible tube 2 in its extended position or when it compresses rubber ring 25 in its withdrawn position, the microprocessor again detects a current increase and stops the motor with an on/off signal. If the time ($t_{on}$)needed to reach this current increase exceeds for example, 5 seconds, the microprocessor triggers an alarm. This control process is depicted in FIG. 3. During execution of the process described in the above example, the control unit, not shown in FIG. 1, causes occlusion device 6 to close. The initial pressure $P_0$ in the tube can be measured by pressure detector 9. Pump 3 can be adjusted for a flow rate close to the maximum flow rate, for example 1,000 ml/h, and the motor preferably is operated for 1.1 revolutions. This operation can last approximately 0.4 seconds. The motor causes rotation of camshaft 6, which activates fingers 7 one after the other by vertical translation. By crimping the tube between fingers 7 and support bracket 5, pump 3 causes displacement of the solution.

The instantaneous pressure $P_i$ then increases in the region situated between pump 3 and occlusion device 8. This pressure increase is measured by pressure detector 9, which produces a voltage signal. The control unit on the implementation device 1 compares the value of the instantaneous pressure to a threshold value. The following equation A must be satisfied, at the latest after completion of 1.1 revolutions.

$$(P_i - P_0) \geq P_1 \text{ where } P_1 = Q_1 \times (P_{1bar} - P_{0bar}) \tag{A}$$

Parameter $Q_1$ can be statistically determined using data from several pumps of the same type. For example, $Q_1$ can be about 0.7. Once a complete cycle has been made and equation A has been satisfied, the motor is stopped. If equation A is not satisfied after 1.1 revolutions of the motor, the control unit triggers an alarm and the process is stopped. If the pressure doesn't reach the threshold value, this indicates that the pump is not operating correctly. This could be the case, for example, if support bracket 5 is broken or a finger 7 on pump 3 no longer blocks the tube. In the case, the solution flows through the line from the pump where an over pressure exists. The threshold pressure can't be reached, therefore, until 1.1 programmed revolutions have been completed.

Once this part of the process is completed successfully, the control unit adjusts the flow rate of pump 3 to an intermediate value, such as, for example, 100 ml/h. The motor preferably is then started for 1.1 revolutions, an operation that preferably requires approximately 4 seconds. The instantaneous pressure is measured throughout this operation, and the minimum and maximum values are calculated. At the end of this operation, the minimum $P_{min}$, and maximum $P_{max}$ values for instantaneous pressure must satisfy equations B and C below:

$$(P_{min}-P_0) \geq P_2 \text{ where } P_2=Q_2 \times (P_{1bar}-P_{0bar}) \quad (B)$$

$$(P_{max}-P_0) \geq P_3 \text{ where } P_3=Q_3 \times (P_{1bar}-P_{0bar}) \quad (C)$$

Parameters $Q_2$ and $Q_3$ can be statistically determined using data from several pumps of the same type. For example, they can be respectively on the order of about 0.6 and 1.2. If either of these two equations is not satisfied, an alarm is triggered because when the minimum value falls below threshold $P_2$, this indicates a loss of pressure. If threshold $P_3$ is not reached, it is possible that during this operation a failure of pump 3 to create a blockage went unnoticed during the first part of the control process, because of the higher rotational speed of the motor and lower pressure in the tube.

The instantaneous pressure in the tube preferably should never exceed the threshold value $P_4$, which indicates excessive over pressure in the system. If equation D being is satisfied, the motor stopped and an alarm is generated.

$$(P_i-P_0) \geq P_4 \text{ where } P_4=Q_4 \times (P_{1bar}-P_{0bar}) \quad (D)$$

Parameter $Q_4$ can be statistically determined using data from several pumps of the same type. For example, $Q_4$ can be about 2.5.

Figure 4:
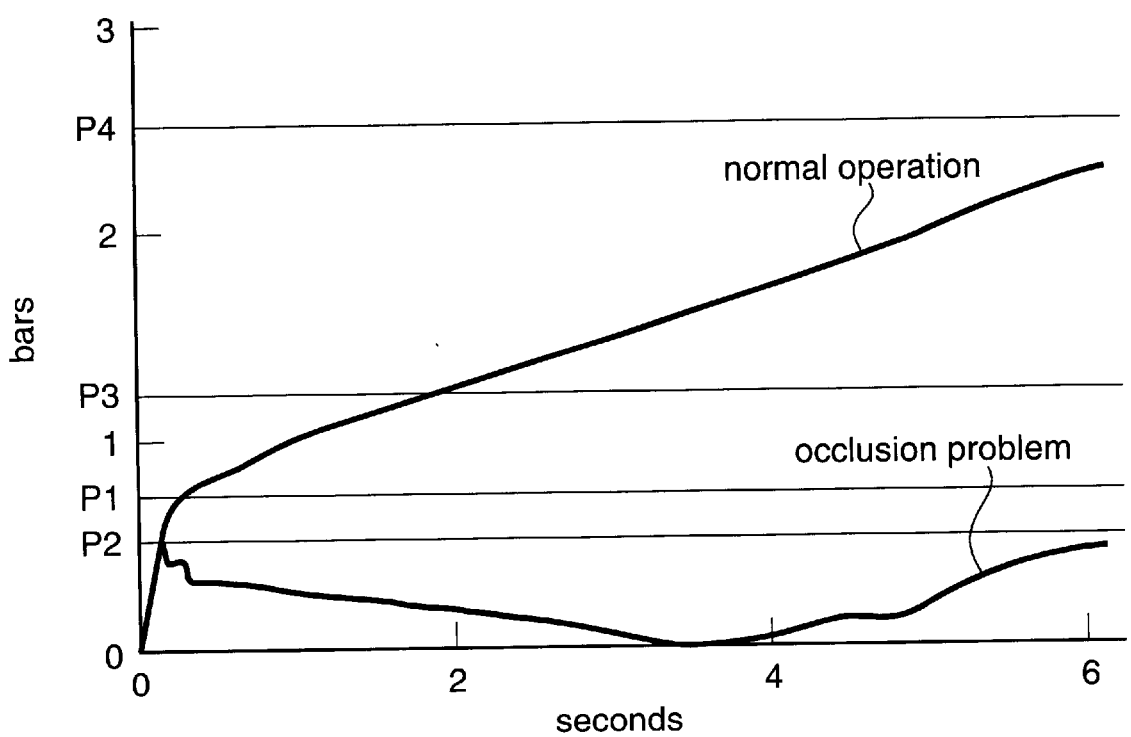
FIG. 4 is a plot showing different instantaneous pressure curves measured during the control process in accordance with the invention.

The different criteria are shown in the plots of FIG. 4, which show an example of a pressure curve for a correctly operating system, and an example of a pressure curve for a system with an occlusion defect.

When the entire process is successfully completed, the control unit causes the pump to turn in the opposite direction for the exact number of cycles it made during the previous steps, to eliminate the over pressure in the section of tube 2 located between pump 3 and occlusion device 8 Occlusion device 8 is then opened.

During execution of the control process, as well as during infusion, pressure detector 10, located upstream of the pump, controls the pressure in the section of the tube located between the recipient containing the solution being administered and the pump. Detector 10 is used to detect a blockage or a rupture of this section of the tube, both of which result in a decrease in pressure.

When the tube is equipped with an automatic arrow-shaped clamp 11, the clamp can only be inserted in the body of pump 3 in one direction. Accordingly, the risk of reversing the position of tube 2 in pump 3 is considerably diminished.

If the length of the section of tube located between the last finger 7 of pump 3 and occlusion device 8)is known, along with the diameter and elastic of the tube, by measuring $P_{max}$ one can verify that tube 2 positioned in pump 3 corresponds to the tube that has been programmed into the pump.

If equations A, B, and C are not satisfied, this indicates either that an underflow situation resulting from, for example, a blockage of the tube upstream of the pump or poor positioning of tube 2)in pump 3 has occurred, or that an overflow situation resulting from, for example, a faulty blockage in a region of pump 3 or poor positioning of tube 2 in said pump 3 has occurred.

Continuous measurement of the pressure upstream and downstream of pump 3 by means of pressure detectors 9 and 10 can be used to detect a blockage of the tube during infusion between the vessel containing the solution and the pump, as well as between the pump and the patient. Rupture of the tube upstream of the pump can also be detected by pressure detector 10. The presence of a device such as automatic clamp 11 prevents tube 2 from being inserted backwards in pump 3.

The process according to the invention can thus be used to satisfy the same functions as a state-of-the-art drop detector, without the drawbacks of that design.

What is claimed is:

1. A process for controlling a pumping device that comprises a pump equipped with a flexible tube, the process comprising the steps of:

blocking said flexible tube by an occlusion device located downstream of said pump;

starting said pump;

measuring an instantaneous pressure in a section of said flexible tube situated between said pump and said occlusion device;

adjusting said pump to provide a flow rate substantially equal to a maximum flow;

performing a predetermined number of cycles, said number of cycles being at least equal to 1;

stopping the pump; and triggering an alarm if the instantaneous pressure does not reach a threshold pressure value after the predetermined number of cycles.

2. The process according to claim 1, further comprising, in the event that the alarm is not triggered, the steps of:

performing with said pump a number of predetermined cycles at least equal to 1;

stopping said pump;

capturing a minimum pressure and a maximum pressure reached during the measuring step; and triggering the alarm if one of the minimum pressure and maximum pressure do not reach respectively a minimum threshold value and a maximum threshold value.

3. The process according to claim 2, further comprising the step of triggering the alarm of the instantaneous pressure reaches a threshold value while performing the number of cycles.

4. The process according to claim 1, further comprising operating said pump in reverse direction for the predetermined number of cycles and re-opening the occlusion device if the alarm is not triggered.

5. A process for controlling a pumping device that comprises a pump equipped with a flexible tube, the process comprising the steps of:

blocking said flexible tube by an occlusion device located downstream of said pump;

starting said pump; and measuring an instantaneous pressure in a section of said flexible tube situated between said pump and said occlusion device;

wherein said pump is a finger pump.

6. A control device for a pumping device with a pump, comprising:

a flexible tube introduced into the pump;

an occlusion device located downstream of said pump;

a first pressure detector located between said pump and said occlusion device for measuring an instantaneous pressure; and a second pressure detector located upstream of said pump.

7. A control device for a pumping device with a pump, comprising:
- a flexible tube introduced into the pump;
- an occlusion device located downstream of said pump;
- a pressure detector located between said pump and said occlusion device for measuring an instantaneous pressure; and
- a control unit adapted to control opening and closing of the occlusion device, to adjust a flow rate of the pump, to operate the pump for a predetermined number of forward and reverse cycles, to analyze the measured instantaneous pressure, and to stop the pump when an alarm is generated.

8. A control device for a pumping device with a pump, comprising:
- a flexible tube introduced into the pump;
- an occlusion device located downstream of said pump, wherein the occlusion device comprises a motor and a head portion driven by the motor, the head portion being adapted to compress the flexible tube; and
- a pressure detector located between said pump and said occlusion device for measuring an instantaneous pressure.

9. The control device according to claim 8, wherein the motor is an electric motor.

10. The control device according to claim 8, wherein the head portion is moved by the motor through a screw drive.

11. An infusion device to administer solutions to patients comprising:
- a flexible tube to carry the solutions;
- a pump propelling the solutions through the flexible tube;
- a first pressure detector to measure pressure in the flexible tube upstream of the pump;
- a second pressure detector to measure pressure in the flexible tube downstream of the pump;
- an occlusion device disposed downstream of the pump, to occlude the flexible tube by varying amounts; and
- a controller for processing data from the first and second pressure detectors and for controlling the occlusion device.

12. The infusion device according to claim 11, wherein the pump is a finger-type pump.

13. A control device for a pumping device with a pump, comprising:
- a flexible tube introduced into the pump, wherein said flexible tube includes an automatic arrow-shaped clamp;
- an occlusion device located downstream of said pump; and
- a pressure detector located between said pump and said occlusion device for measuring an instantaneous pressure.

* * * * *